(12) United States Patent
Shiokawa

(10) Patent No.: US 7,340,295 B2
(45) Date of Patent: Mar. 4, 2008

(54) METHOD AND APPARATUS FOR ESTIMATION OF MUSCLE MASS

(75) Inventor: Takashi Shiokawa, Tokyo (JP)

(73) Assignee: Tanita Corporation, Tokyo (JP)

( * ) Notice: Subject to any disclaimer, the term of this patent is extended or adjusted under 35 U.S.C. 154(b) by 700 days.

(21) Appl. No.: 10/843,396

(22) Filed: May 12, 2004

(65) Prior Publication Data

US 2004/0236245 A1  Nov. 25, 2004

(30) Foreign Application Priority Data

May 21, 2003  (JP)  ............... 2003-143981

(51) Int. Cl.
*A61B 5/05* (2006.01)
*A61B 5/00* (2006.01)

(52) U.S. Cl. .................... 600/547; 600/300

(58) Field of Classification Search ........... 600/300, 600/546, 547
See application file for complete search history.

(56) References Cited

U.S. PATENT DOCUMENTS

| | | | |
|---|---|---|---|
| 3,316,896 A * | 5/1967 | Thomasset | 600/547 |
| 4,008,712 A * | 2/1977 | Nyboer | 600/547 |
| 5,335,667 A | 8/1994 | Cha et al. | |
| 5,372,141 A * | 12/1994 | Gallup et al. | 600/547 |
| 5,579,782 A * | 12/1996 | Masuo | 600/547 |
| 6,643,542 B1 | 11/2003 | Kawanishi | |
| 6,643,543 B2 | 11/2003 | Takehara et al. | |
| 2003/0216665 A1 * | 11/2003 | Masuo et al. | 600/547 |
| 2004/0077968 A1 * | 4/2004 | Simond et al. | 600/547 |

FOREIGN PATENT DOCUMENTS

| | | |
|---|---|---|
| EP | 0 998 875 A1 | 5/2000 |
| EP | 1 201 187 A1 | 5/2002 |
| JP | 10-14899 | 1/1998 |
| WO | WO 01/15600 | 3/2001 |
| WO | WO 02/36004 A1 | 5/2002 |
| WO | WO 03/030735 A1 | 4/2003 |

OTHER PUBLICATIONS

DeLorenzo, A., et al. "Determination of Intracellular Water by Multifrequency Bioelectrical Impedance." Ann Nutr Metab, 1995;39, pp. 177-184, XP008034499.

Janssen, Ian., et al. "Estimation of skeletal muscle mass by bioelectrical impedance analysis." Journal of Applied Physiology 89;2000, pp. 465.471.

* cited by examiner

*Primary Examiner*—Max Hindenburg
*Assistant Examiner*—John Pani
(74) *Attorney, Agent, or Firm*—McDermott Will & Emery LLP

(57) ABSTRACT

The impedance of intracellular water ($Z_{ICW}$), height (H), weight (W), and age (A) of the subject are included as variables in an equation that estimates muscle mass (MM). Impedance of extracellular water ($Z_{ECW}$) is determined by a step of applying an alternating current to the body and measuring the resulting impedance. Impedance of total body water ($Z_{TBW}$) is determined by a step of applying a high frequency alternating current to the body and measuring the resulting impedance. $Z_{ICW}$ is determined by calculating an inverse of the result of subtracting an inverse of measured $Z_{ECW}$ from an inverse of measured $Z_{TBW}$. The equation for muscle mass is of the form: $MM = aH^2/Z_{ICW} + bW + cA + d$.

8 Claims, 8 Drawing Sheets

METHOD AND APPARATUS FOR ESTIMATION OF MUSCLE MASS

BACKGROUND OF THE INVENTION

1. Field of the Invention

The present invention relates to method and apparatus for estimating muscle mass of a subject, and more particularly to, method and apparatus for readily estimating muscle mass with higher precision by mitigating any effect of extracellular water which may introduce some error in estimation of muscle mass.

2. Prior Art

There have been known many types of method of measuring muscle mass of a subject, an example of which is: Magnetic Resonance Imaging (hereafter referred to as "MRI"); Computer Tomography ("CT"); Dual Energy X-ray Absorptiometry ("DEXA"); and the like. Although the technique of MRI, CT and DEXA can provide precise measurement for muscle of the subject it requires very large scale apparatus and facilities, which makes impractical an application of such technique to small scale medical facilities or consumer devices for home use. Additionally, because of X-ray used in CT and DEXA there may be some possibility of exposure to X-ray.

Recently, a muscle estimation and calculation method has been proposed in which a weak alternating current is applied to a body of a subject and bioelectrical impedance is measured, based on which muscle mass is estimated and calculated. In particular, in this method, amount of water contained in the body (hereafter referred to as "total body water") of the subject is calculated based on the measured bioelectrical impedance, and then, a fat free mass is calculated on the basis of the amount of total body water thus calculated. Thereafter, bone mass which is also calculated based on the bioelectrical impedance is subtracted from the fat free mass to produce a value which is considered as the muscle mass. This method can successfully be performed in more simple apparatus and facility than that for the case of MRI, CT and DEXA, as described above, so that it is suitable for use in small scale medical facility or even at home (see Patent Document 1, for example).

The patent document associated with the present invention is as follows:

Patent Document 1: International Laid-Open No. 01/015600 (page 23)

The total body water generally consists of intracellular water that is present inside a cell membrane and extracellular water that is present outside the cell membrane. The extracellular water tends to greatly vary in amount depending on daily life of a person such as water intake, sweating, urination, etc., as compared to the intracellular water. Therefore, the method of estimating muscle mass based on the amount of total body water that is resulted from bioelectrical impedance, as described above, has such tendency that the result of estimation produced thereby depends on the amount of extracellular water at that moment (this is called "fluctuations within a day"), which makes difficult the precise estimation.

In view of the above it is an object of the present invention to provide method and apparatus for estimating muscle mass as simply as possible with higher precision by mitigating any effect of extracellular water which may introduce some error in estimation of muscle mass.

SUMMARY OF THE INVENTION

To attain such object the present invention provides a method of estimating muscle mass, comprising steps of:
measuring impedance of intracellular water of a subject; and
estimating muscle mass of the subject, based on the measured impedance of intracellular water.

According to one embodiment of the present invention said step of estimating muscle mass of the subject further includes sub-steps of:
acquiring personal data including height, body weight and age of the subject; and
calculating muscle mass of the subject according to a predetermined estimation formula using the acquired personal data and the measured impedance of intracellular water as the variables.

According to another embodiment of the present invention said predetermined estimation formula is expressed as follows:

$$MM = a \times Ht^2 / Z_{ICW} + b \times Wt + c \times \text{Age} + d \quad (1)$$

where "MM"=muscle mass of the subject;
"Ht"=height of the subject;
"Wt"=body weight of the subject;
"Age"=age of the subject;
"$Z_{ICW}$"=impedance of intracellular water of the subject; and
"a", "b", "c" and "d"=constant.

According to further embodiment of the present invention said step of measuring impedance of intracellular water of a subject further includes sub-steps of:
measuring impedance of extracellular water of the subject by applying between the predetermined parts of the subject an alternating current at such lower frequency that it only flows outside a cell membrane of the subject;
measuring impedance of total body water of the subject by applying between the predetermined parts of the subject an alternating current at such higher frequency that it flows both outside and inside the cell membrane of the subject; and
calculating the impedance of intracellular water of the subject, which is equal to an inverse of the value derived by subtracting an inverse of the measured impedance of extracellular water from an inverse of the measured impedance of total body water.

According to yet further embodiment of the present invention said predetermined parts of the subject include both feet.

According to yet further embodiment of the present invention said predetermined parts of the subject include a hand and a foot.

According to yet further embodiment of the present invention said predetermined parts of the subject include both hands.

In another aspect the present invention provides an apparatus for estimating muscle mass, comprising: a measurement unit; and an estimation unit, wherein
said measurement unit measures impedance of intracellular water of a subject, and
said estimation unit estimates muscle mass of the subject, based on the measured impedance of intracellular water.

According to one embodiment of the present invention said estimation unit further includes: a personal data acquisition sub-unit; and a muscle mass calculation sub-unit, wherein said personal data acquisition sub-unit acquires personal data including height, body weight and age of the subject, and said muscle mass calculation sub-unit calculates muscle mass of the subject according to the predetermined estimation formula using the acquired personal data and the measured impedance of intracellular water as the variables.

According to another embodiment of the present invention said predetermined estimation formula is expressed as follows:

$$MM = a \times Ht^2/Z_{ICW} + b \times Wt + c \times Age + d \quad (1)$$

where "MM"=muscle mass of the subject;
"Ht"=height of the subject;
"Wt"=body weight of the subject;
"Age"=age of the subject;
"$Z_{ICW}$"=impedance of intracellular water of the subject; and
"a", "b", "c" and "d"=constant.

According to further embodiment of the present invention said measurement unit further includes: a first measurement sub-unit; a second measurement sub-unit; and a calculation sub-unit, wherein said first measurement sub-unit measures impedance of extracellular water of the subject by applying between the predetermined parts of the subject an alternating current at such lower frequency that it only flows outside a cell membrane of the subject, said second measurement sub-unit measures impedance of total body water of the subject by applying between the predetermined parts of the subject an alternating current at such higher frequency that it flows both outside and inside the cell membrane of the subject, and said calculation sub-unit calculates the impedance of intracellular water of the subject, which is equal to an inverse of the value derived by subtracting an inverse of the measured impedance of extracellular water from an inverse of the measured impedance of total body water.

According to yet further embodiment of the present invention said predetermined parts of the subject include both feet.

According to yet further embodiment of the present invention said predetermined parts of the subject include a hand and a foot.

According to yet further embodiment of the present invention said predetermined parts of the subject include both hands.

BRIEF DESCRIPTION OF THE DRAWINGS

Now, the present invention will be described in more detail with reference to the accompanying drawings, in which.

DESCRIPTION OF THE PREFERRED EMBODIMENTS

Method and apparatus for estimating muscle mass according to the present invention is configured to measure impedance of intracellular water of a subject and to estimate muscle mass based on the measured impedance of intracellular water. Accordingly, any effect of extracellular water that is likely to vary in amount in the daily life can be mitigated to provide highly precise estimation for muscle mass.

Preferably, estimating muscle mass is performed by acquiring personal data including height, body weight and age of the subject, and then, calculating muscle mass according to the predetermined estimation formula using the acquired personal data and the measured impedance of intracellular water as the variables. The predetermined estimation formula is effective to readily implement the method and apparatus for estimation of muscle mass according to the present invention.

Preferably, the predetermined estimation formula is one that is represented by the equation (1). After an experiment the present inventor has found that using the estimation equation (1) makes possible to realize highly precise estimation for muscle mass.

Preferably, measuring an impedance of intracellular water is performed by measuring impedance of extracellular water of the subject by applying between the predetermined parts of the subject an alternating current at such lower frequency that it only flows outside a cell membrane of the subject, then, measuring impedance of total body water of the subject by applying between the predetermined parts of the subject an alternating current at such higher frequency that it flows both outside and inside the cell membrane of the subject, and calculating the impedance of intracellular water of the subject, which is equal to an inverse of the value derived by subtracting an inverse of the measured impedance of extracellular water from an inverse of the measured impedance of total body water. Accordingly, the impedance of intracellular water can easily be measured, which makes possible to readily implement the method and apparatus for estimation of muscle mass according to the present invention.

Furthermore, it is recognized that the present invention provides highly precise estimation for muscle mass irrespective of whether the predetermined parts of the subject are both feet, a hand and a foot, or both hands.

Figure 1:
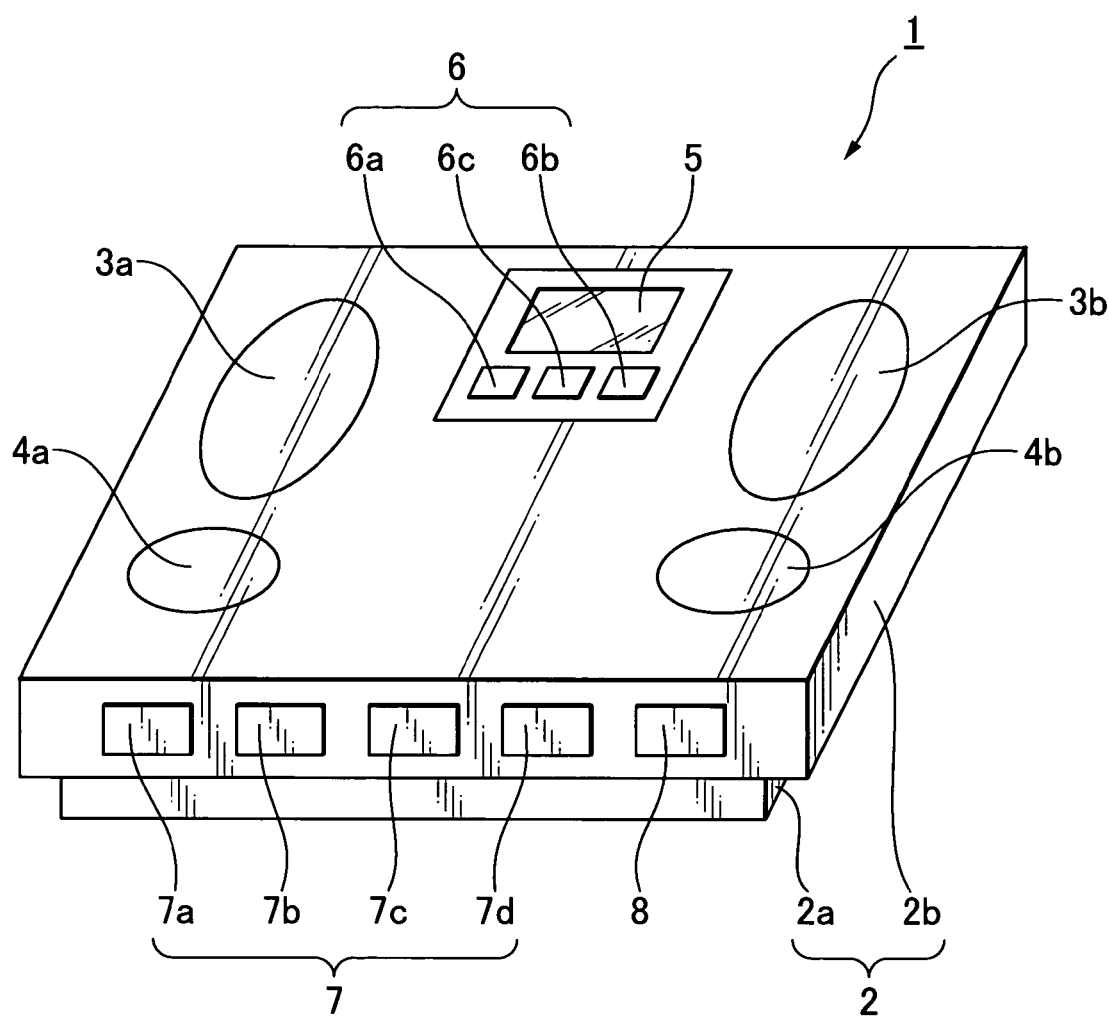
FIG. 1 is an external perspective view of an estimation apparatus for estimating muscle mass according to an embodiment of the present invention.
Figure 2:
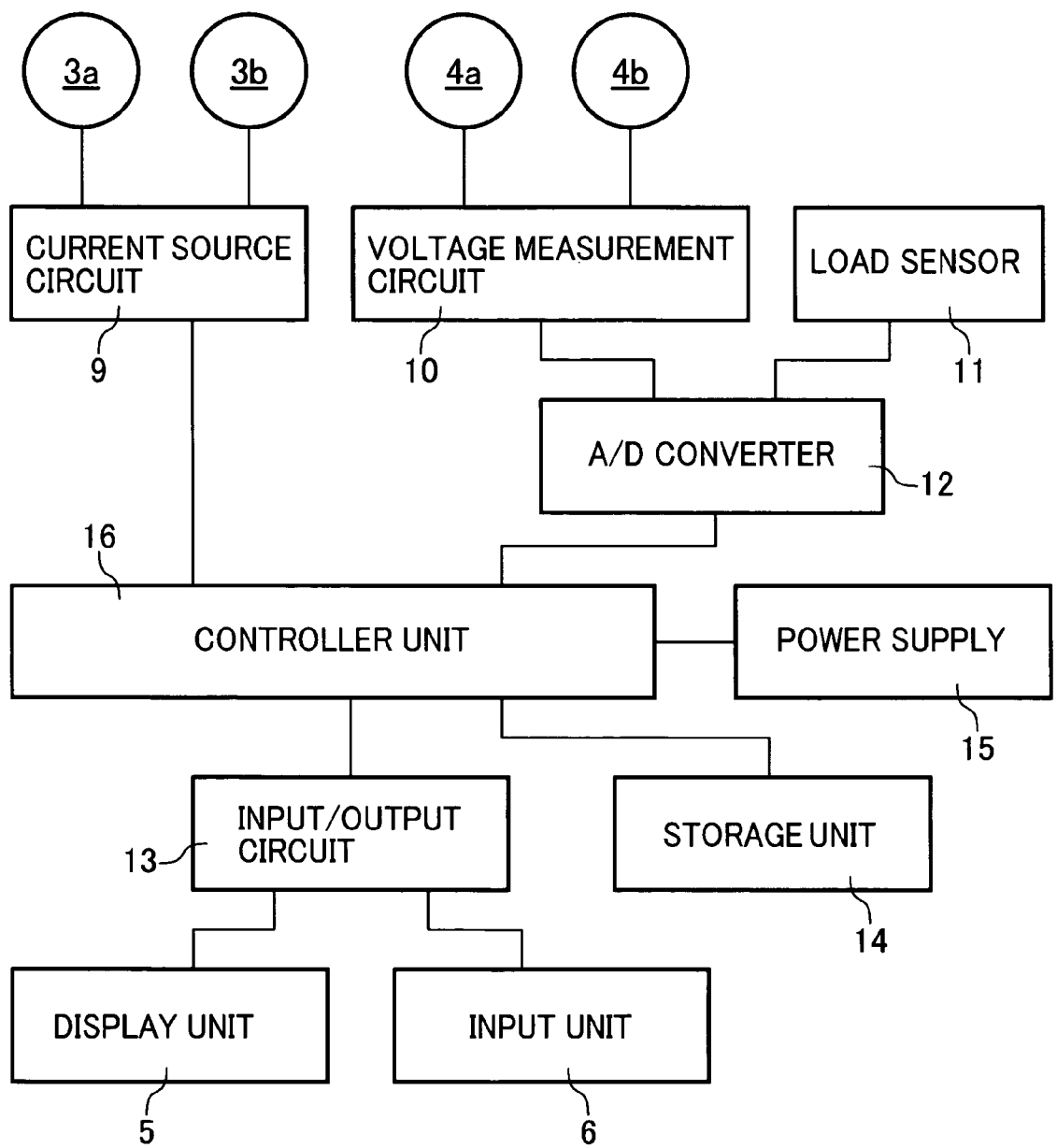
FIG. 2 is a block diagram of electrical circuit elements included in the estimation apparatus in FIG. 1.
Figure 3:
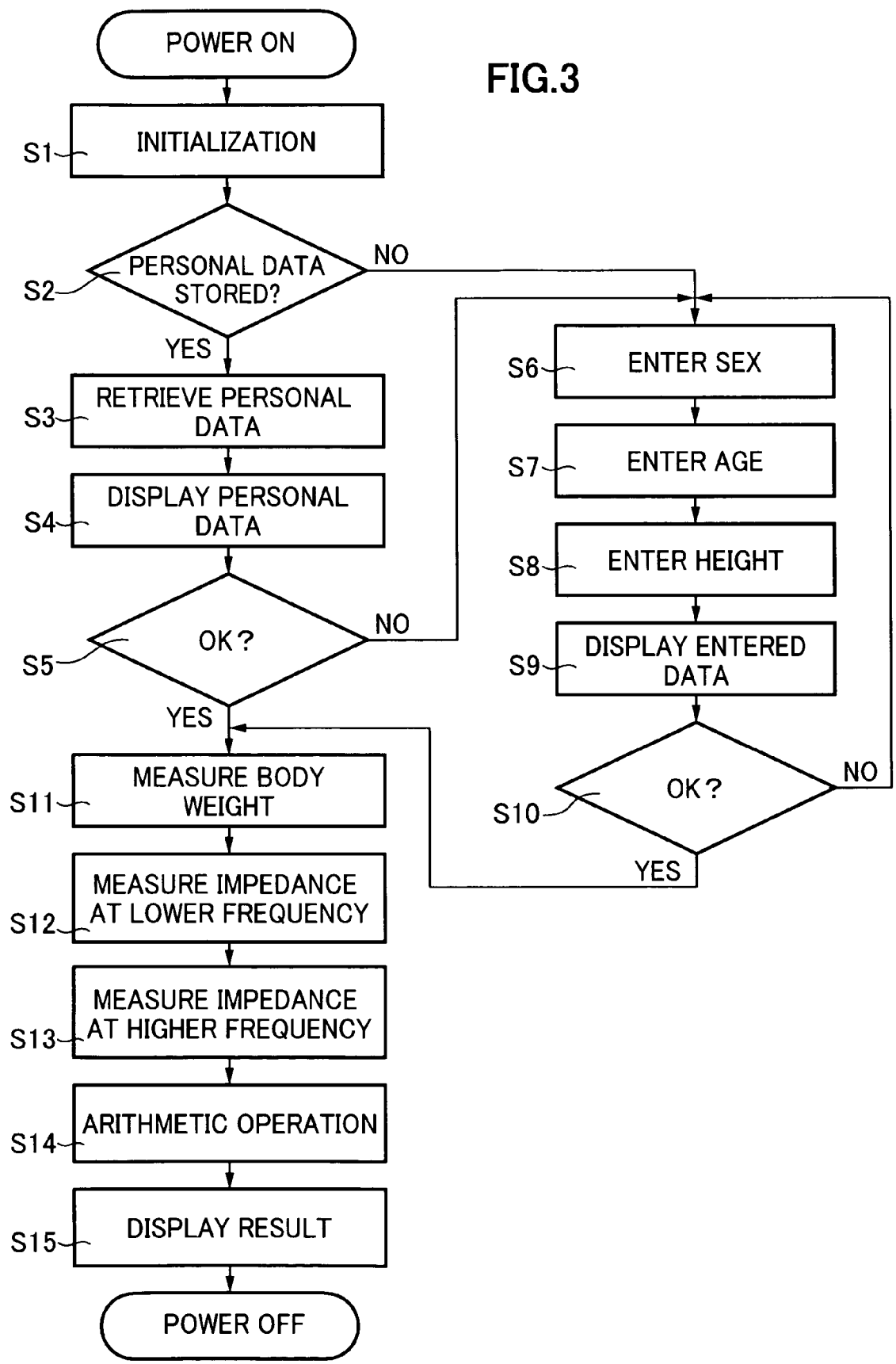
FIG. 3 is a flow chart illustrating a sequence of control steps executed by the estimation apparatus in FIG. 1.

Referring to the drawings, FIG. 1 is an external perspective view of an estimation apparatus 1 for estimating muscle mass according to the present invention, which is intended to implement a method of estimating muscle mass according to the present invention. FIG. 2 is a block diagram of electrical circuit elements included in the estimation apparatus 1. FIG. 3 is a flow chart illustrating a sequence of control steps executed by the estimation apparatus 1. FIGS. 4 to 8 are graphs each illustrating the result of experiment that the present inventor has conducted using the estimation apparatus 1 in order to demonstrate the advantage of the present invention.

Referring to FIG. 1, the estimation apparatus 1 for estimating muscle mass comprises a body 2 consisting of a base 2a and a platform 2b mounted on the base 2a. Provided on the top surface of the platform 2b are: current supplying electrodes 3a, 3b for applying alternating current to a subject between the predetermined parts of his/her body; voltage measurement electrodes 4a, 4b for measuring the voltage (potential difference) across the predetermined parts of the subject while applying alternating current thereto; a display unit 5 made up of prior art liquid crystal screen and the like for displaying muscle mass estimated by the apparatus 1; and an input unit 6 for entering sex, age, height, etc of the subject (hereafter referred to as "personal data"). In particular, the input unit 6 includes select keys 6a, 6b for selecting input data and an enter key 6c for entering the selected input data. In addition, a personal key set 7 consisting of four keys 7a, 7b, 7c, 7d for retrieving the personal data, if already stored in the apparatus, is provided on a side surface of the body 2, together with a power key 8.

Referring to FIG. 2, provided within the body 2 of the estimation apparatus 1 are: a current source circuit 9 connected to the current supplying electrodes 3a, 3b; a voltage measurement circuit 10 connected to the voltage measurement electrodes 4a, 4b; a load sensor 11 for outputting the voltage in response to the load applied thereto; an A/D converter 12 for converting the voltage from the voltage measurement circuit 10 and the load sensor 11 into digital signal; an input/output circuit 13 connected to the display unit 5 and the input unit 6; a storage unit 14 for storing the personal data entered, the body weight measured, the muscle mass estimated, etc.; a power supply unit 15 including batteries; and a controller unit 16 electrically connected to the current source circuit 9, the A/D converter 12, the input/output circuit 13, the storage unit 14 and the power supply unit 15.

In such circuit configuration the controller unit 16 includes a prior art arithmetic element (CPU) which executes a control program stored in the storage unit 14 in advance for providing various control operations in order to control, for example:

sequential supply of alternating current at two frequencies as described later to the current supplying electrodes 3a, 3b;

measurement of bioelectrical impedance of a subject depending on the alternating current and the voltage detected by the voltage measurement electrodes 4a, 4b;

estimation and calculation of the muscle mass of the subject based on the bioelectrical impedance, the personal data of the subject entered by the input unit 6, and the body weight of the subject measured by the load sensor 11; and storage of the personal data entered, the body weight measured, and the muscle mass estimated to the storage unit 14.

Referring to FIG. 3, when the subject depresses the power key 8 for turning ON the apparatus 1 for estimating muscle mass then the controller unit 16 initializes the entire apparatus 1 at step S1. Then, the data, timer count, etc. temporally stored in the storage unit 14 at previous control process operation is initialized.

Thereafter, when the subject depresses any one of the personal keys 7a, 7b, 7c, 7d, at step S2, the controller unit 16 checks to determine whether the personal data associated with the personal key depressed is stored in the storage unit 14 or not. If so, at step S3, the personal data is retrieved, and at step S4, it is displayed on the display unit 5, together with some selection elements (e.g. words "Yes" and "No") for confirmation by the subject. Then, at step S5, if the personal data on the display unit is affirmed by the subject using the selection keys 6a, 6b and the enter key 6c on the input unit 6 then the routine proceeds to step S11. However, if there is no personal data stored in the storage unit 14, as determined at step S2, or if the personal data on the display unit is negated by the subject, at step S5, then the routine proceeds to step S6.

At step S6, the controller unit 16 operates to display a message on the display unit 5 for prompting the subject to enter sex. Then, the subject operates the input unit 6 to enter his/her sex and the routine proceeds to step S7. At this step S7 a message is displayed on the display unit 5 for prompting the subject to enter age. After the subject enters his/her age via the input unit 6 the routine proceeds to step S8. At this step S8 a message is displayed on the display unit 5 for prompting the subject to enter height. When the subject enters his/her height via the input unit 6 the routine proceeds to step S9. At this step S9 the personal data for the subject that have been entered at steps S6 to S8 is displayed on the display unit 5, together with the selection elements for confirmation by the subject, as in the case of step S4. Then, at step S1, if the personal data on the display unit is affirmed by the subject using the input unit 6 then the personal data currently displayed is stored in the storage unit 14 as the personal data corresponding to the personal key that the subject has depressed. Then, the routine proceeds to step S11. However, if, at step S10, the personal data on the display unit is negated the routine returns to step S6.

At step S11 the controller unit 16 instructs to display a message on the display unit 5 for prompting the subject to stand on the platform 2b with the sole of left foot at the tiptoe side contact with the current supplying electrode 3a, the sole of left foot at the heel side contact with the voltage measurement electrode 4a, the sole of right foot at the tiptoe side contact with the current supplying electrode 3b, and the sole of right foot at the heel side contact with the voltage measurement electrode 4b. In response to the message, the subject stands on the platform 2b, and then, the controller unit 16 operates to measure the body weight of the subject, based on the voltage detected by the load sensor 11.

Next, at step S12, the controller unit 16 operates to apply alternating current at frequency of 4 kHz to the subject between his/her both feet from the current source circuit 9 via the current supplying electrodes 3a, 3b, and to detect the voltage (potential difference) across the both feet of the subject through the voltage measurement electrodes 4a, 4b via the voltage measurement circuit 10, thereby measuring bioelectrical impedance of the subject on the basis of applied current and detected voltage according to Ohm's law. It is well known that alternating current at lower frequency on the order of 4 kHz flows outside a cell membrane of living body. Therefore, the bioelectrical impedance, as measured using such lower frequency, is considered to represent the impedance of extracellular water of the subject.

Thereafter, at step S13, the controller unit 16 operates to apply alternating current at frequency of 256 kHz to the subject between his/her both feet from the current source circuit 9 via the current supplying electrodes 3a, 3b, and to detect the voltage across the both feet of the subject through the voltage measurement electrodes 4a, 4b via the voltage measurement circuit 10, thereby measuring bioelectrical impedance of the subject on the basis of applied current and detected voltage according to Ohm's law. It is also known that alternating current at higher frequency on the order of 256 kHz flows both outside and inside the cell membrane of living body. Therefore, the bioelectrical impedance, as measured using such higher frequency, is considered to represent the impedance of total body water made up of extracellular water and intracellular water of the subject.

Then, at step S14, the controller unit 16 operates to calculate the impedance of intracellular water of the subject, based on the impedance of extracellular water, as measured in step S12, and the impedance of total body water, as measured in step S13, and to calculate the muscle mass of the subject, based on the calculated impedance of intracellular water as well as height, body weight and age of the subject.

In order to get the impedance of intracellular water of the subject it is assumed that the subject's body is formed by a parallel circuit consisting of impedance of intracellular water ($Z_{ICW}$) and impedance of extracellular water ($Z_{ECW}$) and that the total impedance for the parallel circuit equals to impedance of total body water ($Z_{TBW}$). Accordingly, it is apparent that an inverse of the impedance of total body water is equal to an inverse of impedance of intracellular water added to an inverse of impedance of extracellular water (i.e. $1/Z_{TBW}=1/Z_{ICW}+1/Z_{ECW}$). On the basis of such relation it is easy to calculate the impedance of intracellular water by producing an inverse of the value derived by subtracting an inverse of impedance of extracellular water from an inverse of impedance of total body water.

The muscle mass of the subject can be derived according to the predetermined estimation formula using the impedance of intracellular water as well as height, body weight and age of the subject as the variables, preferably the estimation formula given by the equation (1) as described above. It has been found that using such estimation formula given by the equation (1) enables higher precision estimation of muscle mass, as will be described with reference to FIGS. 4 to 8.

The estimation formula given by the equation (1) has been provided as follows: First of all, for each of several subjects, dose of radiation from radioactive isotope (potassium) slightly contained in the body is measured to determine amount of potassium in the body. Then, amount of extracellular water for each person is determined, based on the amount of potassium in the body, by taking into account of the fact that the ratio of amount of potassium in extracellular water to that in intracellular water is kept constant. On the other hand, for each of said several subjects, fat free mass is measured according to prior art DEXA technique, and the amount of extracellular water, as determined from the amount of potassium in the body as described above, is subtracted from the fat free mass to determine muscle mass for each subject. Then, multiple regression analysis for the muscle mass for each subject determined in such manner as well as height, body weight, age, bioelectrical impedance (impedance of intracellular water), etc. for each same subject is performed to produce a regression formula given by the equation (1).

In the estimation apparatus 1 as preferred embodiment of the present invention, the calculation program for each of the arithmetic operations as above is stored in the storage unit 14 in advance, and the controller unit 16 executes the calculation program at step S14 to estimate and calculate the muscle mass of the subject.

Then, at step S15, the controller unit 16 operates to display the body weight, as measured at step S11, and the muscle mass, as estimated and calculated at step S14, on the display unit 5 for predetermined time period. Thereafter, the controller unit 16 turns OFF power to terminate all the control operations.

Figure 4:
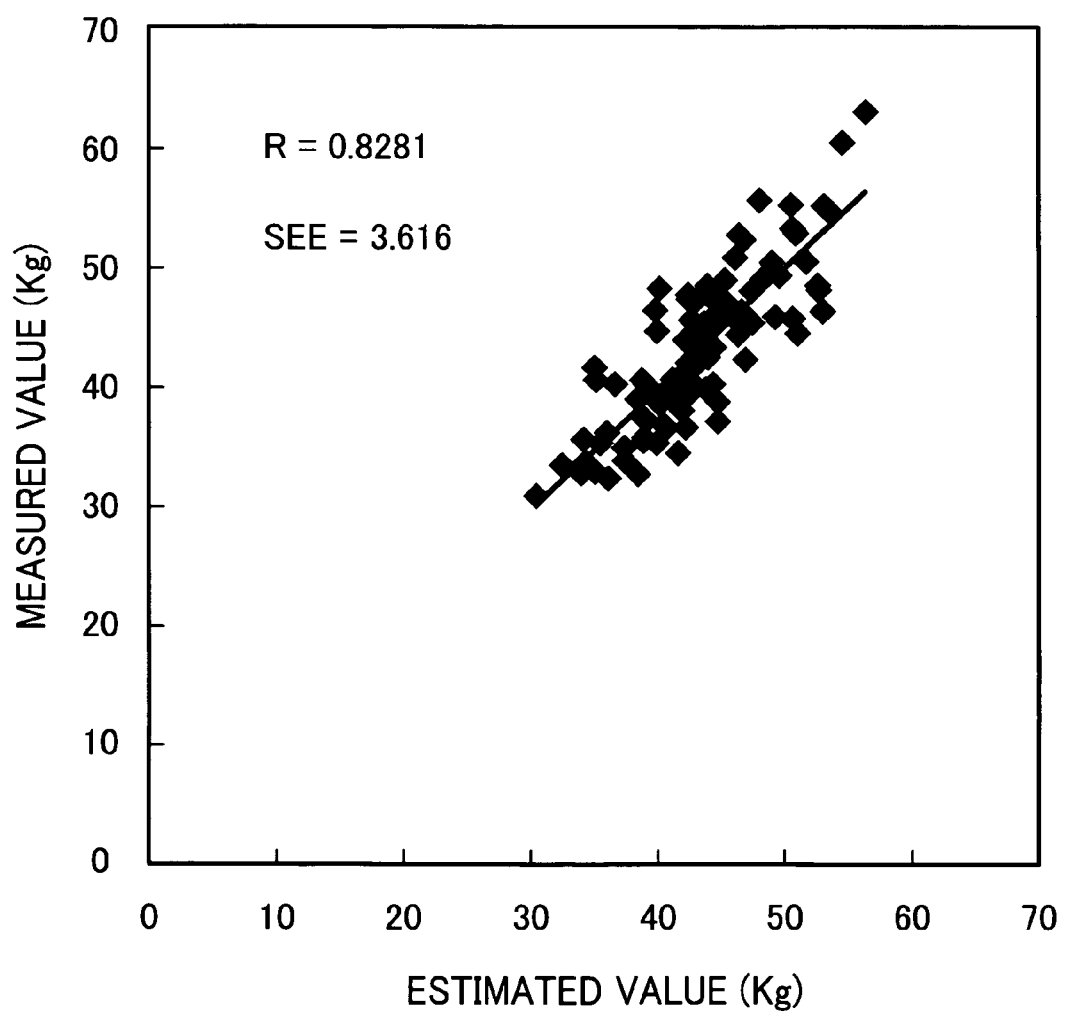
FIG. 4 is a graph showing correlation between muscle mass as estimated by the estimation apparatus in FIG. 1 and that as measured by prior art DEXA.
Figure 5:
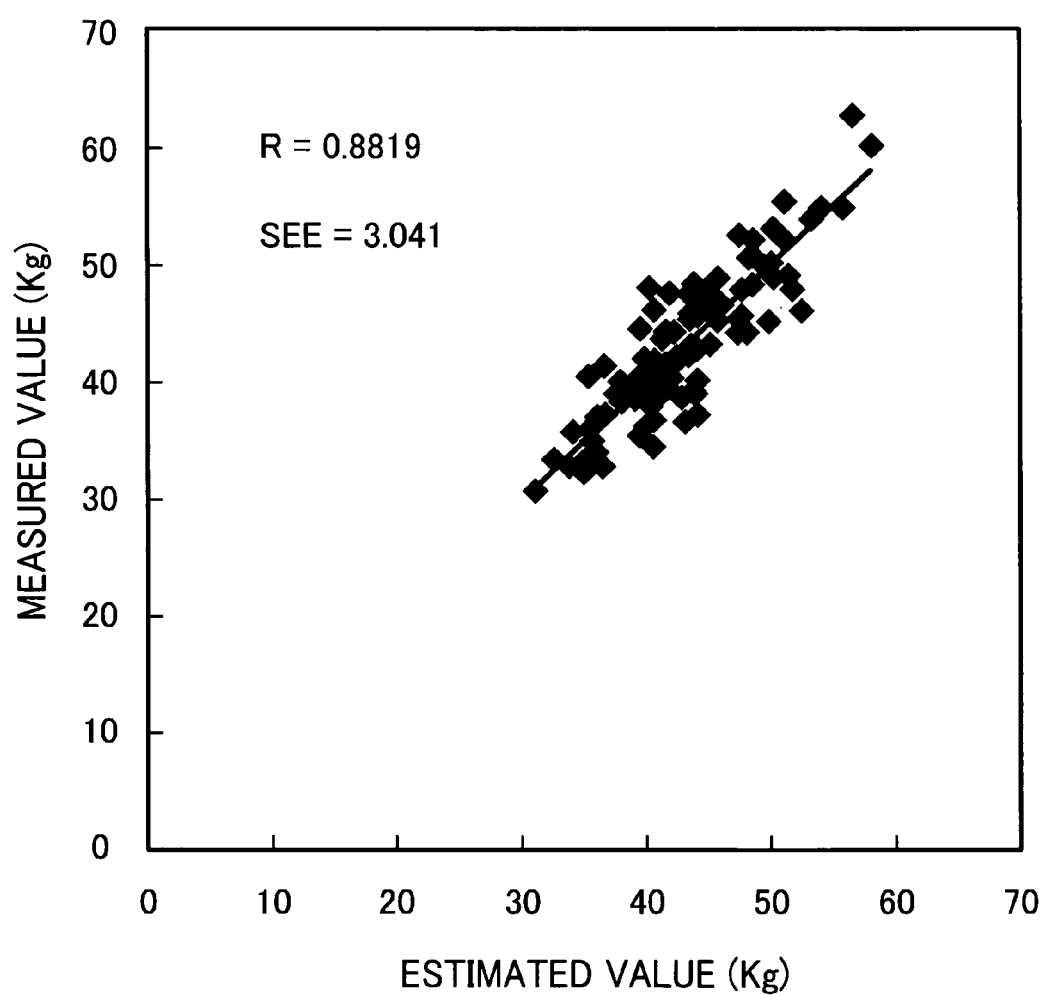
FIG. 5 is another graph showing correlation between muscle mass as estimated by the estimation apparatus in FIG. 1 and that as measured by prior art DEXA.
Figure 6:
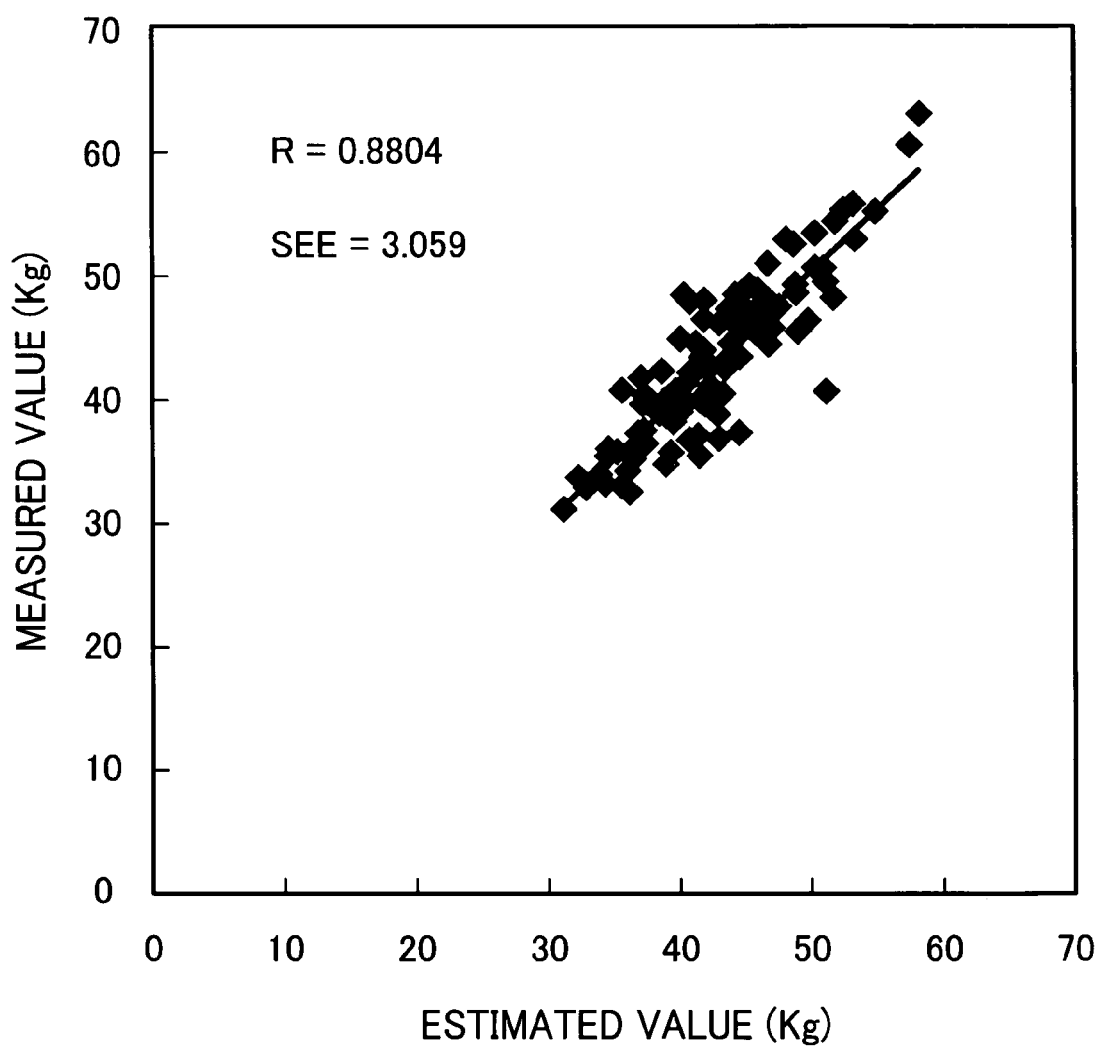
FIG. 6 is further graph showing correlation between muscle mass as estimated by the estimation apparatus in FIG. 1 and that as measured by prior art DEXA.

FIGS. 4, 5 and 6 each plots, for several subjects, the muscle mass as estimated by the estimation apparatus 1 according to the embodiment on the horizontal axis and the muscle mass as measured on the basis of the amount of potassium in the body, as described above, on the vertical axis in order to illustrate correlation between them. That is to say, the estimated muscle mass on the horizontal axis is derived in such manner that the impedance of extracellular water and the impedance of total body water are measured by using alternating current at lower frequency of 4 kHz and at higher frequency of 256 kHz, as described above, to derive the impedance of intracellular water which is then used to estimate and calculate the muscle mass according to the equation (1). In this respect it is noted that FIG. 4 plots the estimated muscle mass in case where alternating current is applied to the subject between his/her both feet, as described above. In contrast thereto, FIG. 5 plots the estimated muscle mass in case where alternating current is applied between a hand and a foot of the subject, and FIG. 6 plots in case where alternating current is applied between both hands of the subject.

Figure 7:
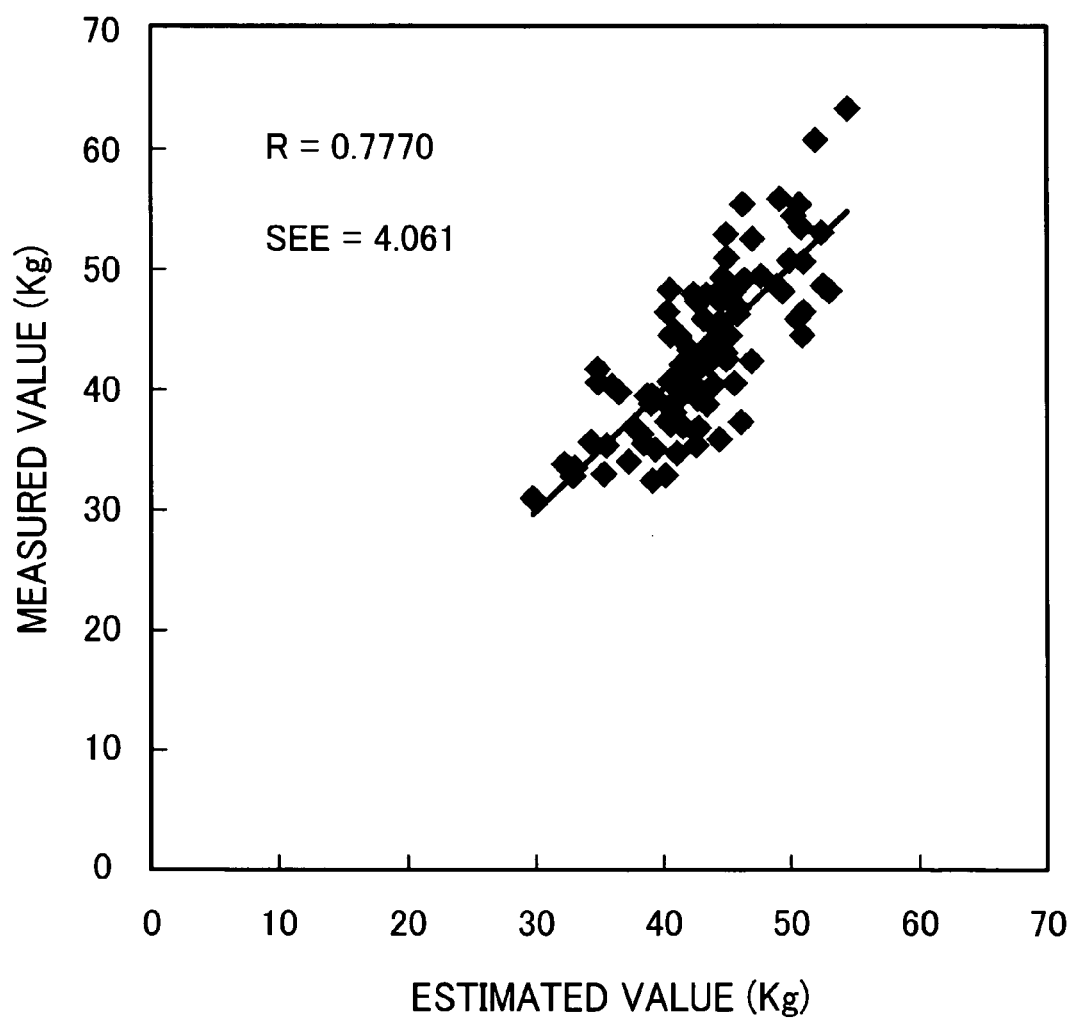
FIG. 7 is a graph showing correlation between muscle mass as estimated by a previous estimation apparatus for estimating muscle mass and that as measured by prior art DEXA.

On the other hand, FIG. 7 plots, for the same several subjects, the muscle mass as estimated using the prior art estimation apparatus on the horizontal axis and the muscle mass as measured on the basis of the amount of potassium in the body, as described above, on the vertical axis in order to illustrate correlation between them. In this case, the estimated muscle mass on the horizontal axis is derived in such manner that alternating current at single frequency of 64 kHz is applied to the subject between his/her both feet to measure the bioelectrical impedance, on the basis of which the amount of total body water, fat free mass and bone mass are calculated, and finally, the bone mass is subtracted from the fat free mass to estimate and calculate the muscle mass.

Comparison of Correlation Coefficient "R" that is defined to represent degree of correlation between the estimated muscle mass and the measured muscle mass is made among the cases of FIGS. 4 to 7. In particular, for the case of FIG. 4 "R"=0.8281; for FIG. 5 "R"=0.8819; for FIG. 6 "R"=0.8804; and for FIG. 7 "R"=0.7770. Comparison of Standard Error of Estimation "SEE" is also made among the cases of FIGS. 4 to 7. For the case of FIG. 4 "SEE"=3.616; for FIG. 5 "SEE"=3.041; for FIG. 6 "SEE"=3.059; and for FIG. 7 "SEE"=4.061. It is needless to say that as Correlation Coefficient "R" approaches to 1 higher correlation is present between the estimated muscle mass and the measured muscle mass, while as Standard Error of Estimation "SEE" becomes smaller there is lesser error between the estimated muscle mass and the measured muscle mass. It is apparent from comparison between FIGS. 4 and 7 that the muscle mass as estimated by the estimation apparatus 1 has higher correlation to the muscle mass as measured on the basis of the amount of potassium in the body than the muscle mass as estimated by prior art estimation apparatus, thereby providing highly precise estimation for muscle mass. It is also apparent from FIGS. 5 and 6 that higher precision estimation for the muscle mass can provided irrespective of whether the bioelectrical impedance (impedances of extracellular water and total body water) is measured between both feet, or a hand and a foot, or both hands.

Figure 8:
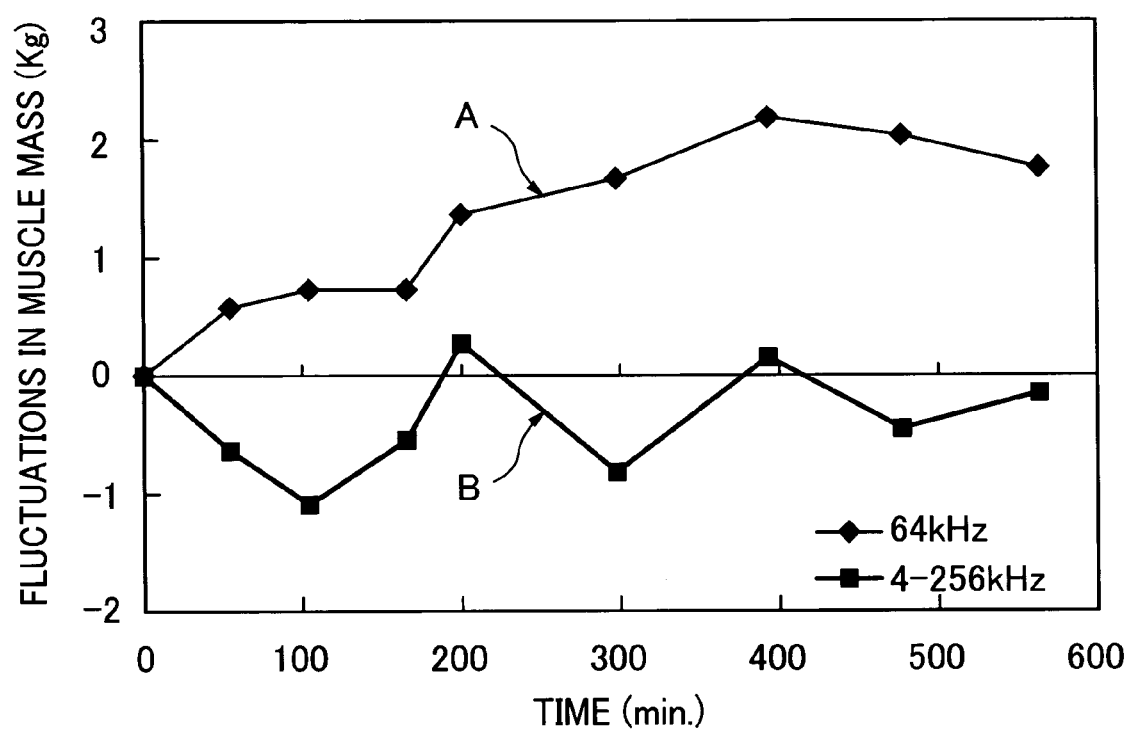
FIG. 8 is a graph showing fluctuations in muscle mass within a day as estimated by the estimation apparatus in FIG. 1 and by the previous estimation apparatus.

FIG. 8 is a graph illustrating fluctuations in muscle mass within a day (a curve B) as estimated by the estimation apparatus 1 according to the present invention and that (a curve A) as estimated by the prior art estimation apparatus. Time that has elapsed since the first estimation is plotted on the horizontal axis, and amplitude of fluctuations relative to the first estimated muscle mass is plotted on the vertical axis. It is noted that the estimation apparatus 1 of the present invention and the prior art estimation apparatus both have measured the bioelectrical impedance of the same subject between his both feet. It is apparent in FIG. 8 that the estimation apparatus 1 of the present invention in which the impedance of intracellular water of the subject is measured for the purpose of mitigating any effect of the amount of extracellular water (see the curve B) has smaller fluctuations in estimated muscle mass as compared to the prior art estimation apparatus in which the muscle mass is estimated based on the amount of total body water including the extracellular water (see the curve A), thereby minimizing any fluctuations in estimated muscle mass within a day.

One embodiment of the present invention has been described above with reference to the accompanying drawings. However, the present invention is not necessarily be limited to such embodiment, but may be embodied in many other forms. For example, the estimation apparatus 1 may be configured in such manner that the display unit 5 and the input unit 6 are separately provided from the body 2 and an electrical cable or wireless communication such as infrared is used for connection therebetween. Furthermore, the number of personal keys 7 may be greater than or smaller than four (4) and each of personal keys 7a, 7b, 7c and 7d may also have function of power key. In addition, entering of height data may be done not only by the input unit 6, but also by a height meter such as an electronic measure that is provided to the body 2 for measuring the height of the subject. Alternatively, the load sensor 11 may be omitted from the body 2, and instead, the body weight of the subject may be entered via the input unit 6.

In addition to the muscle mass of the subject the estimation apparatus 1 may be configured to produce additional body composition data such as fat mass, percent fat, visceral fat area, visceral fat mass, body water amount, body water percent, bone mass, basal metabolism, etc. using the measurement of bioelectrical impedance.

The electrodes for measuring bioelectrical impedance of the subject have been described above as being provided on the top of the body 2 of the estimation apparatus 1 for measuring bioelectrical impedance between both feet of the subject. Alternatively, some hand electrodes configured to be held by both hands of the subject for measuring bioelectrical impedance therebetween may be used. Furthermore, a set of foot and hand electrodes for measuring bioelectrical impedance therebetween may be used. It may additionally be possible that so called eight-electrode system consisting of right and left foot electrodes as well as right and left hand electrodes is provided for estimating and calculating the muscle mass for each of body parts of the subject such as right arm, right leg, left arm, left leg, etc. Or alternatively, the electrodes for measuring bioelectrical impedance of the subject may be configured in such manner that a small sized portable type housing is used for the body 2 and electrodes are mounted on the housing for contact with a finger or palm of the subject. In addition, the electrodes configured to be affixed on the skin of the body may be placed on any parts of the body to measure the bioelectrical impedance therebetween (for example, between shoulder and elbow and between back of knee and heel).

Furthermore, the present invention may be embodied in such manner that the bioelectrical impedance is measured using alternating current at each of not less than three frequencies ranging from lower frequency to higher frequency, instead of using alternating current at two frequencies in the above described embodiment, to produce the bioelectrical impedance vector which is then used to derive the impedance of intracellular water.

It is apparent from the foregoing that method of estimating muscle mass according to the present invention is configured to measure impedance of intracellular water of a subject and to estimate muscle mass based on the measured impedance of intracellular water, whereby any effect of extracellular water, of which amount is likely to vary in the daily life, can be mitigated to provide highly precise estimation for muscle mass.

Estimation of muscle mass is performed by acquiring personal data including height, body weight and age of the subject, and then, calculating muscle mass according to the predetermined estimation formula using the acquired personal data and the measured impedance of intracellular water as the variables. This greatly facilitates estimation of muscle mass.

The predetermined estimation formula is one that is represented by the equation (1), which makes possible to realize highly precise estimation for muscle mass.

Measurement of impedance of intracellular water is performed by measuring impedance of extracellular water of the subject by applying between the predetermined parts of the subject an alternating current at such lower frequency that it only flows outside a cell membrane of the subject, then, measuring impedance of total body water of the subject by applying between the predetermined parts of the subject an alternating current at such higher frequency that it flows both outside and inside the cell membrane of the subject, and calculating the impedance of intracellular water of the subject, which is equal to an inverse of the value derived by subtracting an inverse of the measured impedance of extracellular water from an inverse of the measured impedance of total body water. Accordingly, the impedance of intracellular water can easily be measured, which makes possible to readily implement estimation of muscle mass.

Furthermore, the present invention provides highly precise estimation for muscle mass irrespective of whether the predetermined parts of the subject are both feet, a hand and a foot, or both hands.

It is also apparent that an apparatus for estimating muscle mass according to the present invention comprises: a measurement unit; and an estimation unit, wherein said measurement unit measures an impedance of intracellular water of a subject, and said estimation unit estimates muscle mass of the subject, based on the measured impedance of intracellular water, whereby the apparatus can mitigate any effect of extracellular water, of which amount is likely to vary in the daily life, to provide capability of highly precise estimation for muscle mass.

Furthermore, said estimation unit further includes: a personal data acquisition sub-unit; and a muscle mass calculation sub-unit, wherein said personal data acquisition sub-unit acquires personal data including height, body weight and age of the subject, and said muscle mass calculation sub-unit calculates muscle mass of the subject according to the predetermined estimation formula using the acquired personal data and the measured impedance of intracellular water as the variables. Such configuration greatly facilitates estimation of muscle mass.

The predetermined estimation formula is one that is represented by the equation (1), which makes possible to realize highly precise estimation for muscle mass.

Moreover, said measurement unit further includes: a first measurement sub-unit; a second measurement sub-unit; and a calculation sub-unit, wherein said first measurement sub-unit measures an impedance of extracellular water of the subject by applying between the predetermined parts of the subject an alternating current at such lower frequency that it only flows outside a cell membrane of the subject, said second measurement sub-unit measures an impedance of total body water of the subject by applying between the predetermined parts of the subject an alternating current at such higher frequency that it flows both outside and inside the cell membrane of the subject, and said calculation sub-unit calculates the impedance of intracellular water of the subject, which is equal to an inverse of the value derived by subtracting an inverse of the measured impedance of extracellular water from an inverse of the measured impedance of total body water. Accordingly, the measurement unit for measuring the impedance of intracellular water can easily be embodied, which makes possible to readily implement the apparatus for estimation of muscle mass.

Furthermore, the present invention provides the apparatus capable of highly precise estimation for muscle mass irrespective of whether the predetermined parts of the subject are both feet, a hand and a foot, or both hands.

What is claimed is:

1. A method of estimating muscle mass, comprising steps of:
    calculating an impedance of intracellular water of a subject; and
    estimating a muscle mass of the subject, based on the impedance of intracellular water;
    wherein said step of estimating a muscle mass of the subject further includes the sub-steps of acquiring personal data including height, body weight and age of the subject, and calculating muscle mass of the subject according to a predetermined estimation formula using the acquired personal data and the impedance of intracellular water as variables;
    wherein said predetermined estimation formula is expressed as follows:

$$MM=(a*H^2)/Z_{ICW}+b*W++c*A+d$$

wherein MM is the muscle mass of the subject; H is the height of the subject; W is the body weight of the subject; A is the age of the subject; and a, b, c, d are constants;
    wherein said step of calculating impedance of intracellular water of a subject further includes sub-steps of:
    measuring impedance of extracellular water of the subject by applying between predetermined parts of the subject an alternating current at a sufficiently low frequency that the current only flows outside a cell membrane of the subject;
    measuring impedance of total body water of the subject by applying between the predetermined parts of the subject an alternating current at sufficiently high frequency that the current flows both outside and inside the cell membrane of the subject; and
    deriving the impedance of intracellular water of the subject by calculating an inverse of the result of subtracting an inverse of the measured impedance of extracellular water from an inverse of the measured impedance of total body water.

2. A method of estimating muscle mass according to claim 1 in which said predetermined parts of the subject include both feet.

3. A method of estimating muscle mass according to claim 1 in which said predetermined parts of the subject include a hand and a foot.

4. A method of estimating muscle mass according to claim 1 in which said predetermined parts of the subject include both hands.

5. An apparatus for estimating muscle mass, comprising a measurement unit and an estimation unit,
    wherein said measurement unit calculates an impedance of intracellular water of a subject, and said estimation unit estimates muscle mass of the subject, based on the impedance of intracellular water;
    wherein said estimation unit further includes a personal data acquisition sub-unit and a muscle mass calculation sub-unit, wherein said personal data acquisition sub-unit acquires personal data including height, body weight and age of the subject, and said muscle mass calculation sub-unit calculates muscle mass of the subject according to a predetermined estimation formula using the acquired personal data and the impedance of intracellular water as the variables;
    wherein said predetermined estimation formula is expressed as follows:

$$MM=(a*H^2)/Z_{ICW}+b*W++c*A+d$$

wherein MM is the muscle mass of the subject; H is the height of the subject; W is the body weight of the subject; A is the age of the subject; and a, b, c, d are constants;
    wherein said measurement unit further includes a first measurement sub-unit, a second measurement sub-unit, and a calculation sub-unit, wherein:
    said first measurement sub-unit measures an impedance of extracellular water of the subject by applying between predetermined parts of the subject an alternating current at a sufficiently low frequency that the current only flows outside a cell membrane of the subject,
    said second measurement sub-unit measures impedance of total body water of the subject by applying between the predetermined parts of the subject an alternating current at a sufficiently high higher frequency that the current flows both outside and inside the cell membrane of the subject, and
    said calculation sub-unit calculates the impedance of intracellular water of the subject, by calculating an inverse of the result of subtracting an inverse of the measured impedance of extracellular water from an inverse of the measured impedance of total body water.

6. An apparatus for estimating muscle mass according to claim 5 in which said predetermined parts of the subject include both feet.

7. An apparatus for estimating muscle mass according to claim 5 in which said predetermined parts of the subject include a hand and a foot.

8. An apparatus for estimating muscle mass according to claim 5 in which said predetermined parts of the subject include both hands.

* * * * *